United States Patent [19]

Menyhart

[11] 4,154,590
[45] May 15, 1979

[54] PREPARATION OF PHOTOCHROMIC GRADIENT LENSES

[75] Inventor: Alexander F. Menyhart, Brimfield, Mass.

[73] Assignee: American Optical Corporation, Southbridge, Mass.

[21] Appl. No.: 849,274

[22] Filed: Nov. 7, 1977

Related U.S. Application Data

[62] Division of Ser. No. 657,006, Feb. 10, 1976.

[51] Int. Cl.² ............................ C03C 15/00; C03B 31/00
[52] U.S. Cl. ........................................ 65/30 R; 65/33;
65/111; 65/115; 65/119; 65/DIG. 2; 106/52;
106/DIG. 6
[58] Field of Search ............... 65/30 R, 33, DIG. 2,
65/111, 115, 119; 106/DIG. 6, 52

[56] References Cited

U.S. PATENT DOCUMENTS

| 3,419,370 | 12/1968 | Cramer et al. | 65/30 E |
| 3,795,523 | 3/1974 | Moriya et al. | 65/DIG. 2 |
| 3,833,511 | 9/1974 | Yamashith et al. | 65/DIG. 2 |
| 3,920,463 | 11/1975 | Simms | 65/30 R X |
| 3,938,977 | 2/1976 | Gliemeruth | 65/33 X |

FOREIGN PATENT DOCUMENTS

| 739404 | 7/1966 | Canada | 65/DIG. 2 |
| 1380781 | 1/1975 | United Kingdom | 350/160 P |

*Primary Examiner*—S. Leon Bashore
*Assistant Examiner*—Frank W. Miga
*Attorney, Agent, or Firm*—Jeremiah J. Duggan; Howard R. Berkenstock, Jr.

[57] ABSTRACT

Glass lenses or lens blanks, containing all the ingredients necessary to produce phototropic or photochromic behavior, are treated in a conventional production furnace to produce a locally variable heat treatment, wherein at least one portion thereof is raised to a temperature exceeding the glass strain point but not the softening point, and other portions are heated to variable temperatures decreasing from the strain point. The treatment causes development of phototropic or photochromic behavior only in those portions of the lenses or lens blanks exposed to the temperature above the strain point.

6 Claims, 4 Drawing Figures

SCHEMATIC REPRESENTATION OF APPEARANCE OF A PLANO LENS AND CORRESPONDING VISUAL TRANSMITTANCE ALONG CENTER LINE OF THE SAME LENS BEFORE A AND AFTER B EXPOSURE TO SUNLIGHT.

PREPARATION OF PHOTOCHROMIC GRADIENT LENSES

The present application is a division of application Serial No. 657,006, listed above.

This invention relates to the preparation of lenses or lens blanks having phototropic or photochromic qualities, more particularly to the preparation of such lenses or lens blanks having continuous gradations in the phototropic behavior.

CROSS-REFERENCE TO RELATED APPLICATIONS

This invention provides improvement of the methods of manufacture of such lenses and lens blanks as fully set forth in related patent application Ser. No. 624,688, filed Oct. 22, 1975, abandoned in favor of Ser. No. 668,175 filed Mar. 19, 1976, now U.S. Pat. No. 4,036,624 issued July 19, 1977; pending application Ser. No. 789,585 filed Apr. 21, 1977, now U.S. Pat. No. 4,101,302 issued July 18, 1978; pending application Ser. No. 785,492 filed Apr. 7, 1977; and copending application Ser. No. 657,006 filed Feb. 10, 1976; all assigned to the Assignee of the present application.

BACKGROUND OF THE INVENTION

The related applications, identified above, set out fully the background of the invention and prior art of this invention. The following description briefly sets out some of the background and prior art of the invention, set out in said applications;

Ophthalmic lenses serve basically three purposes;
(1) correction of vision defects
(2) protection against mechanical hazards to the eye; and
(3) protection against radiation.

The first purpose is accomplished with transparent lenses having refractive powers, and the second purpose is accomplished by providing lenses of the required physical strength. The third purpose of protection against radiation such as ultraviolet light, intense visible light or infrared radiation can be achieved by adding color in or on the glass of the lenses or in or on the plastics or polymers of the lenses.

The colored lenses and their preparation are fully described in the above related applications.

Permanently colored or dyed ophthalmic lenses have a disadvantage of retaining low transmission of light in low levels of illumination, that is in a more or less dark environment. In such low light environments as nighttime driving, conventional sunglasses may be hazardous. It has been found that this particular disadvantage may be overcome to a certain extent, by the many varieties of phototropic or photochromic commercially available glass or plastic lenses. U.S. Pat. No. 3,197,396 describes phototropic ophthalmic lenses, containing silver ions, which are transparent to visible radiation but will darken to exposure to actinic radiation to where the transmission will be about 45% of the orignal transmissivity. Some of the other prior art directed to ophthalmic lenses includes U.S. Pat. Nos. 3,208,860; 3,548,060; 3,594,198; 3,617,316; 3,703,388; 3,765,913; 3,795,523; 3,833,511; 3,834,912; British Patent No. 1,275,019; German patent No. 2,230,506; and German Auslegeschrift No. 2,256,775.

In addition to the above mentioned patents on photochromic glasses, all containing silver halide particles uniformly dispersed throughout the volume of an article, it is known that Chance-Pilkington Optical Glass Company, England, it marketing a phototropic phospho-silicate glass under a trade name "Reactolite."

Other photochromic glasses sensitized by silver halides are described in general in the following articles:

W. H. Armistead and S. D. Stookey: "Photochromic Silicate Glasses Sensitized by Silver Halides," SCIENCE, Vol. 144 (1964) pp. 150–154;

G. Gliemeroth and K. H. Mader: "Phototropic Glass," Angew. Chem. Internat. Edit., Vol. 9 (1970) pp. 434–445;

A. V. Dotsenko et al.: "A Study of the Effect of Copper Ions on the Relaxation Properties of Photochromic Glasses," Sov. J. P. Opt. Technol., Vol. 41 (1974) pp. 395–397;

R. J. Araujo: "Photochromic Glasses," Chapter 8 of the book PHOTOCHROMISM edited by G. H. Brown, Willey Interscience, New York (1971) pp. 667–686;

H. Bach and G. Gliemeroth: "Phase Separation in Phototropic Silver-Halide-Containing Glasses," J. Amer. Cer. Soc. (1971) pp. 43–44.

The prior art glasses seem to have in common:
1. the ingredients producing the photochromic or phototropic behavior are silver halide particles uniformly dispersed in a glass matrix; and
2. articles made from these glasses must be exposed to a well defined heat treatment to develop photochromic or phototropic behavior.

The literature described glasses appear to differ from each other in the compositions of the base glasses which serve as carriers for the phototropic or photochromic centers. U.S. Pat. No. 3,208,860 describes a phototropic article comprising a silicate glass body having in at least a portion thereof microcrystals of at least one silver halide selected from the group consisting of silver chloride, silver bromide, and silver iodide, with the concentration of said crystals in the portion being at least 0.005% by volume.

U.S. Pat. No. 3,419,370 teaches a preparation of photochromic lenses by diffusing silver ions into the surface layer of a base glass and then exposing the articles to a specific heat treatment. Glass or plastic articles have also been prepared as photochromic materials by coating the substrates with a phototropic coating as described in U.S. Pat. No. 3,875,321 and described in The Journal of the American Ceramic Society (1974) pps. 332–335 under the title "Reversible Optical Density Changes in Composite Layers."

The photochromic or phototropic lenses above described have certain advantages over permanently tinted lenses. Thus because of the reversibility of the photochromic effect such lenses assume a low transmissivity if exposed to ultraviolet or blue light but resume high transmissivity in an environment where low illumination levels of activating radiation prevail. Glass lenses do not appear to lose photochromic properties as do plastic phototropic lenses during extended wear causing degradation of active ingredients.

All presently known photochromic or phototropic lenses have the disadvantage that recovery of high transmissivity takes several minutes. This has been noticed with discomfort and dislike by wearers under such conditions as driving an automobile where low levels of illumination exist inside the car and high levels of illumination may exist outside the vehicle. While it is desirable to reduce the light intensity to the driver's eyes while observing road and traffic conditions, the driver must be permitted to clearly view information presented by instruments on the vehicle instrument panel where a low level of illumination normally exists. Indeed, it may be dangerous to prevent this. A similar type of problem may be found in occupations where sudden changes in the level of illumination from bright to dim occur either (1) by rapid changes in the intensity of the light source of (2) by movement of the wearer of the spectacles from high level of intensity to a darker environment.

Some of the disadvantages have been overcome by the use of eyeglasses with a continuous variation of transmissivity from low at the top of the lens to high over the lower portion of the lens. Lenses with such a permanent gradient in degree of color or tint are now available in commerce, and it is believed that such lenses are prepared by differentially dyeing plastic lenses or by applying a graded color coating over glass lenses by vacuum deposition of absorbing materials. With plastic lenses such color gradient may be achieved by concentration of the dye absorbed by the lens by different areas. For example, a high concentration of absorption prevails at the top and a low concentration at the bottom of the lens.

In U.S. Pat. No. 3,419,370 there is found a statement that a gradient in photochromic behavior across a glass body is attainable by varying the time and/or temperature at different portions of the glass body exposed to an ion exchange medium. According to this patent the ion exchange bath contains, in all instances, silver ions (see Table 2 of the patent). The gradient in photochromic properties is achieved by causing or allowing different concentrations of silver ions to diffuse into the glass. The teachings of the patent, in my opinion, is that glass cannot be made photochromic or phototropic without having been exposed to the diffusion process in the silver containing ion exchange bath prior to the heat treatment required to develop phototropic or photochromic behavior. The base composition of the glasses do not contain any silver ions, nor is there a teaching of a photochromic gradient over ophthalmic lenses.

In my opinion, the state of the art of making ophthalmic lenses uniformly phototropic or photochromic throughout their entire volume can be summarized as follows:

1. Glasses of the types listed in Table 1 hereafter are melted following procedures known to those skilled in the art of glass making.
2. Lens blanks are made of these glasses by known methods such as pressing or casting.
3. These articles are exposed to a controlled heat treatment to develop silver halide particles of linear dimensions d falling essentially within the range $5 < d < 50$ nm. The lower limit is required to produce photochromic or phototropic behavior, the upper limit to avoid light scattering unacceptable in ophthalmic products. The total concentration of these silver halide particles which are dispersed uniformly throughout the glass article should be at least 0.005 vol. %.

In my opinion, the state of the art of making glass articles with a gradient in photochromic or phototropic behavior as deduced from U.S. Pat. No. 3,419,370 can be summarized as follows:

1. A base glass having a composition in essence in the general system Alk. Oxide—$Al_2O_3$—$B_2O_3$—$SiO_2$, with addition of halides to the batch, is melted under conditions that allow retention of a sufficient quantity of halides.
2. Lens blanks are made from the glasses by known methods such as pressing or casting.
3. Finished lenses are made from the blanks by grinding and polishing.
4. The finished lenses are exposed to a source of silver ions at elevated temperature in such a fashion that in those parts of the lens where a high degree of phototropic or photochromic behavior is desired the silver concentration is higher than in those parts where a low degree of phototropic or photochromic behavior is desired.
5. The thus treated lenses are exposed to a carefully controlled heat treatment to grow silver halide crystals to a size required for photochromic or phototropic behavior, but not exceeding linear dimensions of 50 nm to avoid the light scattering unacceptable in ophthalmic lenses.

SUMMARY OF THE INVENTION

Ophthalmic lens pressings which do not exhibit phototropic or photochromic behavior are made from glasses containing all necessary ingredients to produce such phototropic or photochromic behavior. Such glass is hereafter sometimes referred to as "unnucleated" photochromic glass. This expression is used herein for reasons of simplicity. As clearly pointed out in the related applications, the submicroscopic nuclei required to develop silver halide particles exist in the non-phototropic state of the glass. In other words, the nuclei are so small they cannot be seen with a light microscope since they do not apparently reflect light. Numerically speaking, they have a maximum linear dimension which is less than about 5 nm. As will be recognized by one skilled in the art, these particles are too small to interact with light in the visible spectrum. While the nuclei has not been actually measured, the 5 nm number is chosen as having meaning to one in this art. The pressings are not exposed to the heat treatment required to develop photochromic or phototropic behavior. The pressings are transferred or made into lens blanks, the blanks are given a gradient in their phototropic or photochromic behavior by exposing them to a temperature gradient field. The exposure is such that one portion of the blank is heated to a temperature to above the strain point but below the temperature of the softening point of the glass, while a distance part of the blank is maintained at a temperature below the strain point.

It has also been found that ophthalmic lenses made from unnucleated glass pressings which have been exposed to the specific heat treatment required to develop photochromic or phototropic behavior, can be made into semi-finished or finished lenses having their gradient in their phototropic or photochromic behavior across the face of the lens.

It has been found that so-called "one-piece multifocal" or "raised ledge multifocal" glass lenses and progressive power glass lenses with desirable properties can be made with a gradient in the phototropic or photochromic behavior since such lens designs are particularly suited to the practice of the present invention. The portion of the lens used for distant vision can be made phototropic or photochromic whereas the portion of the lens used for near vision will not have such properties. To achieve such a gradient in photochromic or phototropic behavior, raised ledge multifocal lenses or lens blanks suitable for subsequent generating and polishing are exposed to a temperature gradient as described below, alternatively, finished lenses may be exposed to a corresponding temperature gradient.

The present invention is applicable to glass lens blanks and lenses which contain all of the ingredients required for producing photochromic or phototropic behavior substantially uniformly dispersed throughout the glass body but having silver halide in an unnucleated state, i.e., particles of less size than that required to produce photochromic or phototropic behavior. It is preferred to use glasses with a coefficient of expansion below $60 \times 10^{-7}$ per degree C. to reduce thermal fracture of lenses and blanks during treatment in the temperature gradient field. However, the invention is not limited to such glasses. The invention provides for improvements in selective thermal masking using particulate material by damming the particulate material at the region between the masked and unmasked portion of said lens blank to provide for the progressive heat gradation resulting from suppression of furnace heat by the masking.

DESCRIPTION OF THE PREFERRED EMBODIMENT

To better understand the processes according to the instant invention, the above related applications contain a full description of the transmission of lenses, generally as follows:

The transmission T of a glass lens can be described by the expression $$T = \exp(-K \cdot Z_0)$$

where
- $K$ = coefficient of extinction and
- $Z_0$ = thickness of the lens at the location of measurement measured parallel to the direction of the incident beam of light.

K is a function of the wavelength of light and for a given wavelength is normally a material constant characteristic for the glass the lens is made of. The lens thickness $Z_0$ is a variable of the two space coordinates x and y in a plane normal to the optical axis of the lens. The degree of variation of $Z_0$ depends on the Rx values of the lens. For negative lenses $Z_0$ is larger at the edge than at the center, for positive lenses $Z_0$ is larger at the center than at the edge. This results in a local variation of the light transmission T. Strong negative lenses e.g. made of a colored glass appear to be darker at the edge than at the center. The degree of variation of T in this case is entirely determined by the shape of the lens required to achieve a specific prescription. In general, $Z_0 = Z_0(x,y)$.

In case of a photochromic or phototropic lens the extinction coefficient K is time dependent and dependent upon wavelength and intensity of the activating radiation. For reasons of simplicity a monochromatic activating radiation of constant intensity shall be assumed. If t is the duration of exposure to such activating radiation $K_1$ increases with t or $$(dK_1/dt) > 0,$$

whereby $K_1(t)$ reaches a constant value after approximately ½ hour depending upon the glass studied and the precision of the measurement.
Therefore eq. (1) becomes $$T_1(T) = e^{-K_1(t) \cdot Z_0}$$

with $$\frac{dT_1}{dt} = -Z \cdot \frac{dK_1}{dt} \cdot e^{-K_1(T) \cdot Z_0} < 0$$

i.e. the transmission decreases with increasing exposure time. The saturation value of $T_1(t)$ reached after approximately 30 minutes can be between 30 and 45% depending upon the nature of the glass and the thickness of the lens. The original transmission before exposing the lens to activating radiation is normally about 90%.

After removing the activating radiation the lens gradually regains its original transmission value. This process can be described by introducing a second time dependent extinction coefficient $K_2(t)$ with $$(dK_2/dt) < 0.$$

Correspondingly the change in transmission $T_2$ with time t is $$\frac{dT_2}{dt} = Z_0 \cdot \left|\frac{dK_2}{dt}\right| \cdot e^{-K_2(t) \cdot Z_0} > 0.$$

In general terms the transmission T of a photochromic lens therefore can be described by $$T(t,x,y) = \exp(-K_i(t) \cdot Z_0(x,y))$$

with $K_i(t) = K_1(t)$ during exposure to activating radiation, and
$K_i(t) = K_2(t)$ after removing the activating radiation;
$Z_0(x, y)$ is determined by the prescription values required to provide for correction of vision in each individual case.

To achieve a gradient in phototropic or photochromic behavior across the face of a lens the coefficient of extinction K must be a function of the two space coordinates x and y in addition to its dependence of time:

$$K = K(t,x,y).$$

The corresponding expression for light transmission through the lens at a point x,y is $$T(t,x,y) = \exp(-K(t,x,y) \cdot Z_0(x,y)).$$

which for plano lenses can be simplified to $$T(t,x,y) = \exp(-K(t,x,y) \cdot Z_0)$$

with $Z_0$ = constant.

To achieve such a space dependent coefficient of extinction prior art U.S. Pat. No. 3,419,370 teaches utilization of a corresponding variation in the concentration of silver required to form silver halide crystals providing for phototropic or photochromic behavior. As indicated above in the section "Background Discussion of the Prior Art" such a process is only applicable to finished lenses. It is furthermore very difficult to control and requires an additional step; namely, the introduction of silver ions through a diffusion process. It furthermore requires use of a glass melted under special conditions to retain sufficient halogen to form silver halide particles.

Prior workers have failed to recognize or appreciate that all potentially phototropic or photochromic glass articles utilizing silver halide particles to achieve phototropic or photochromic behavior can be used to prepare articles with a gradient in that behavior. To produce an extinction coefficient K(t,x,y) through local variation of the silver concentration the prior workers have used a specially melted glass and subsequent exposure to a silver diffusion process. In contrast we provide a locally variable extinction coefficient through well controlled development of a proper size distribution of silver halide particles in unnucleated glass initially containing all of the necessary silver and halogen atoms uniformly distributed throughout the entire volume of the glass article. Such a desirable size distribution of silver halide particles is achieved by carefully controlled exposure to a locally variable temperature field. This can be done with either lens blanks or finished lenses. Such lenses are made of glass which can be described as "potentially photochromic or phototropic glass."

While practicing the present invention, care must be taken to avoid thermal fracture of the lenses or lens blanks when they are exposed to a locally variable temperature field. Glasses with a low coefficient of thermal expansion, such as certain boro-silicates, are better suited for this application than glasses with a high coefficient of thermal expansion, such as the phosphosilicates. Boro-silicate glasses have coefficients of thermal expansion in the range approximately 30 to $60 \times 10^{-7}/°$ C. To the best of our knowledge other glasses used commercially as a carrier of matrix for photochromic or phototropic centers have coefficients of thermal expansion of $90 \times 10^{-7}/°$ C. and above. The higher the coefficient of thermal expansion, the higher the thermal stresses exiting in the glass article when they are exposed to a temperature gradient.

Figure 1:
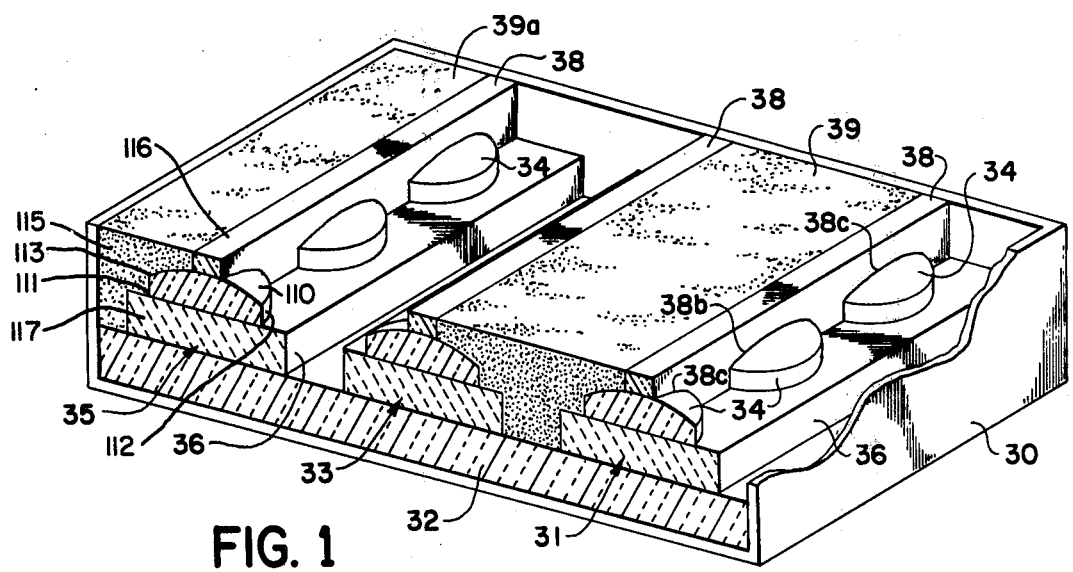
FIG. 1 is a cut-away perspective view of a further modified method for the variated temperature treatment of a plurality of lenses or lens blanks.

By example, illustrated in FIG. 1, a stainless steel fusing tray 30, of dimensions approximately 12 inches long, 6 inches wide and 2½ inches high, has its inside bottom preferably covered with such as a 1-inch asbestos sheet 32. A series of lenses 34, each mounted on a chromite fusing block 36, may be positioned on the asbestos. A strip of asbestos 38 is mounted on each lens or series of lenses in such a manner that the strip 38 forms a dam at about the middle of the lenses. Thus, this strip 38 includes cutouts 38a, 38b and 38c which conform closely to the curvature of the lens blanks so as to rest on the surface of the lens blanks. Between the series of lenses 31 and the series 33 and their positioned or overlying asbestos strip 38 is a bed of conventional glass makers silica of the usual coarse type and of conventional high purity. The high purity is required to ensure low iron content to avoid contamination of the lens blanks, e.g. 200 parts per million or less. The bed should be of sufficient depth to blanket that portion of each of the lenses which is to be heated to a temperature below the strain point, described in the related applications. A second bed of sand 39a is formed between a wall of the tray and the dam 38 in the series 35. Thus, about half of each lens in each series will be exposed to full temperature of the atmosphere of the oven, while a lens under the sand is raised to a lesser temperature. With the lenses, dams, and masking silica mounted in the tray, the tray is passed through a conventional production furnace, providing heating as described above.

Figure 3:
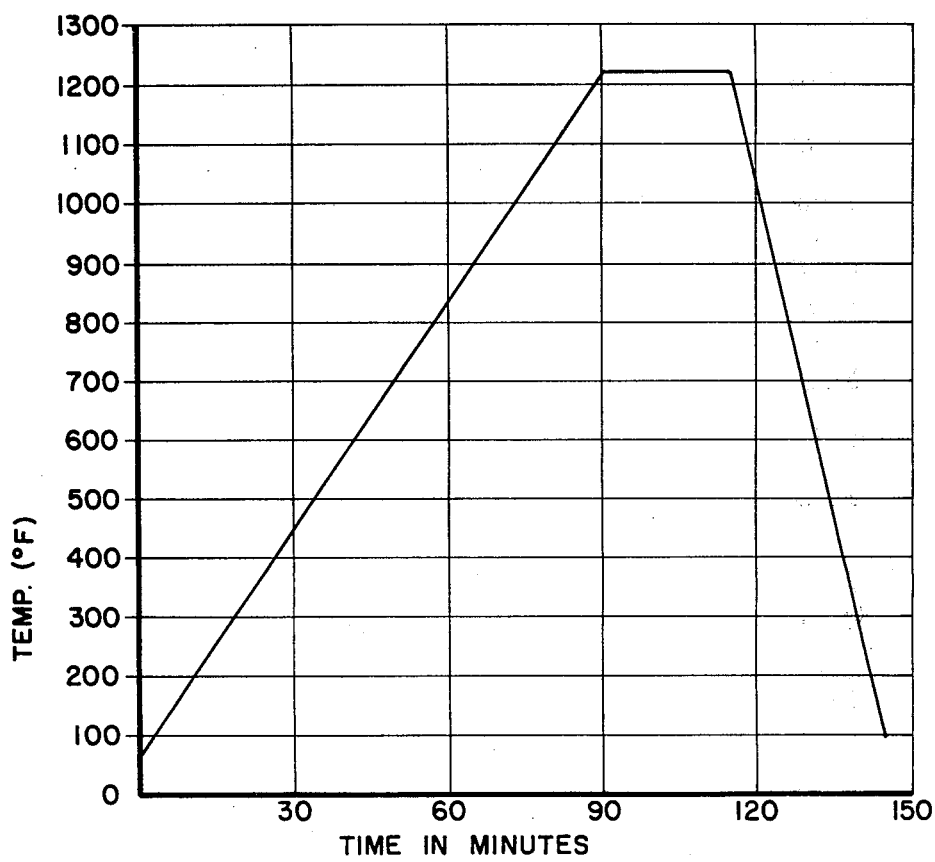
FIG. 3 is a general temperature profile for the time-temperature relationship for producing variable heating of lens portions according to the invention.

The tray with the silica and the mounted lenses and blocks is placed in a conventional production photochromic bifocal furnace, and the temperature is raised to about 1220° F. over a period of 90 minutes. Once the 1220° F. temperature is reached, the assembly with the lenses is permitted to soak at that temperature for about 20 minutes. The lenses are thereafter cooled over a period of about 30 minutes to a temperature where they can be handled, that is about 100° F. The time-temperature profile is shown in FIG. 3.

The masking or insulating material, shown as the coarse grain, glass-makers silica may contain moisture in the form of water. It should be understood, that the sand in the embodiments where the sand is used as a masking material, functions as a heat sink. Moisture in the sand enhances the heat sink characteristics of the sand, since the water must be evaporated to permit the sand to heat much above the boiling point of water. Therefore, the quantity of water to be heated provides a degree of control of the temperature to which insulated or masked portions of each lens is to be subjected. Clearly, the more moisture in the sand, the more heat that is required to vaporize it and thus less heat is transmitted to the lenses. Further, other vaporizable liquids and solids, chemically compatible with the system may be used, for example, petroleum products including various derivative products, waxes, and other high temperature materials may be used. Further, metal particles may be mixed with the sand grains which form the insulated cover to enhance the heat sink characteristics thereof. Refractory grains, other than silica may be used, for example, alumina, chromite, magnesia, calcia, etc. Proper control of size gradation of the grain bed is desirable to assure all voids are filled to the highest practical extent. As will be recognized by those skilled in the refractory art, maximum packing through proper size gradation tends to eliminate trapped air.

In the foregoing, the silver halide particles are mentioned in linear dimensions. It is understood, however, that in discussing particles being smaller than about 5 nm, and which substantially progressively increase in size to about 50 nm, we are describing an average particle. An "average particle" is defined to mean a substantial preponderance of the particles have the specific linear dimensions. Obviously, some particles will be smaller and some will be larger in any given area because of the lack of precise control of the chemical reactions which result in particle formation. Further, while the photochromic material is described as silver chloride, silver bromide, and silver iodide, the silver composition may also be mixture of the same.

Table 1

| Compositions in wt % of Unnucleated Glasses Useable According to This Invention | | | | | |
|---|---|---|---|---|---|
| | A | B | C | D | E |
| $SiO_2$ | 53.0 | 21.4 | 58.8 | 57.3 | 0.0 |
| $Al_2O_3$ | 10.5 | 37.7 | 22.9 | 9.1 | 8.3 |
| $ZrO_2$ | 2.0 | 0.0 | 0.0 | 0.0 | 1.3 |

Table 1-continued

Compositions in wt % of Unnucleated Glasses Useable According to This Invention

|  | A | B | C | D | E |
|---|---|---|---|---|---|
| Li$_2$O | 2.1 | 0.0 | 4.5 | 0.0 | 0.0 |
| BaO | 6.0 | 5.5 | 0.0 | 0.0 | 3.3 |
| SrO | 0.2 | 0.0 | 0.0 | 0.0 | 0.0 |
| Na$_2$O | 0.6 | 3.8 | 1.5 | 6.5 | 16.2 |
| NaF | 1.0 | 1.0 | 4.7 | 3.1 | 0.0 |
| NaCl | 1.0 | 1.0 | 1.8 | 2.6 | 1.0 |
| Ag$_2$O | 0.4 | 0.5 | 0.4 | 0.5 | 0.6 |
| PbO | 5.1 | 0.0 | 0.0 | 1.0 | 0.0 |
| CuO | 0.1 | 0.1 | 0.02 | 0.02 | 0.02 |
| P$_2$O$_5$ | 0.0 | 15.6 | 0.0 | 0.0 | 7.5 |
| B$_2$O$_3$ | 18.0 | 4.8 | 2.5 | 18.6 | 61.8 |
| K$_2$O | 0.0 | 8.6 | 0.0 | 0.0 | 0.0 |
| NaBr | 0.0 | 0.0 | 0.8 | 1.3 | 0.0 |
| MgO | 0.0 | 0.0 | 2.1 | 0.0 | 0.0 |

Colorants well known to those skilled in the art may be included. Such colorants are substantially neutral or non-reactive as far as the other glass constituents are concerned. Exemplary ones include: transition metal oxides including such as Fe$_2$O$_3$, Cr$_2$O$_3$, CoO; certain rare earth oxides such as Nd$_2$O$_3$, Pr$_2$O$_3$.

The glasses specified by the letters A, B, C, D and E of Table 1, may be used to practice the invention. To use the glasses, the lens or lens blanks are prepared. The strain point and the softening point of respective glasses are noted and the furnace is operated to permit an appropriate temperature above the strain point but below the softening point. The masking provides an appropriate temperature gradient along the lens. The appropriate temperature gradient permits a potential upper portion of the lens to have well-developed silver halide crystals, with a controlled progression to substantial freedom from nucleation at the bottom or potential bottom of the lenses or lens blanks. There is thus established a graded thermal masking of the lenses, or lens blanks. The maximum masking is over that area which is to serve as the reading, or bottom, portion of the lens, or lens blank, when it is glazed in a frame. There is substantially no masking over that area which is to serve as the distance portion and thus there is thermally introduced maximum nucleation. As mentioned above, the sand bath 21 serves as a heat sink thereby assisting in providing the progressive thermal gradient. This method is accomplished, of course, by assuring that the leading edge of a lens is heated about its strain point but below its softening point, while the masked portion is heated to a lower temperature. After heating, the lenses are permitted to sufficiently cool to avoid thermal fracture by conventional procedures. Further, conventional grinding, polishing, generating, edging and glazing techniques may be used to prepare and mount the lenses in frames. Suitable conventional strengthening techniques, pursuant to commercial practices, may be used to satisfy government regulations.

Figure 4:
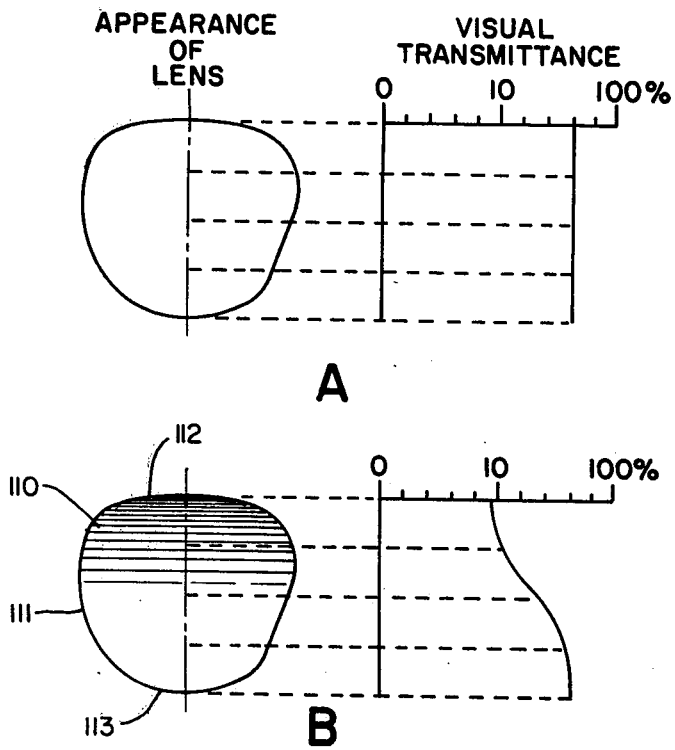
FIG. 4 is a schematic representation of the appearance of a plano lens and the corresponding visual transmittance across the face of such a lens before (a) and after (b) exposure to activating radiation (sunlight) for approximately 30 minutes.
Figure 2:
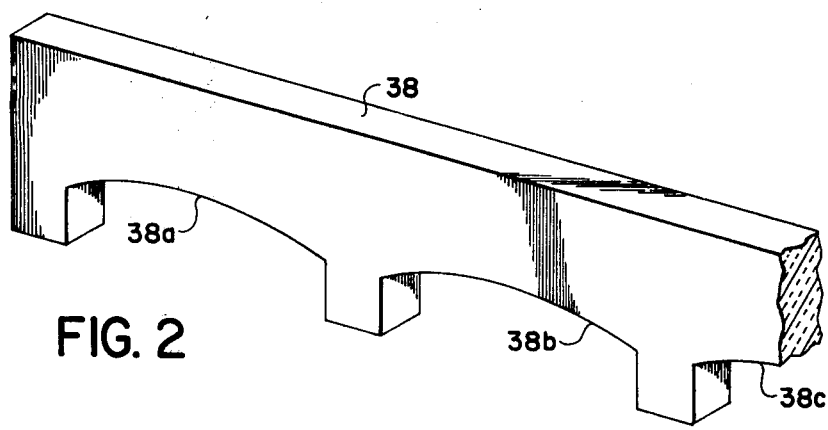
FIG. 2 is a partial perspective view of element 38 of FIG. 1.

As shown in FIG. 4, section A demonstrates transmittance of a plano lens when in its unactivated condition. Section B illustrates the gradient of transmittance of the lens after it has been exposed to sunlight for a period of time. This schematically shows the results of the lens or lens blank treatment according to the invention.

Broadly speaking, an article fabricated according to the present invention is a lens or lens blank exhibiting regressive variation in photochromic behavior from top to bottom as the lens appears in a frame. Distributed throughout the oxide glass body from which the lens or blank is fabricated are silver halide particles consisting of about at least 0.005 vol. % thereof. The silver halide particles in the finished lens are of such a size distribution that in at least one portion of the article the linear dimension of the particles are smaller than about 5 nms and their remaining portion of the article range between 5 and 50 nm. Thus, at the top, or through the portion referred to as the distance portion, the particles are relatively large whereas in the lower or reading portion of the lens the particles are progressively smaller than about 5 nm. As shown in FIG. 7 there is a schematic representation of a lens prepared according to the present invention, wherein there is a gradation of size of silver halide particles from bottom, having the smallest particles, to the top having the largest particles due to the particular type of heating. In the lens shown in portion A, the lens has not been subjected to actinic light and the visual transmittance is about 75%. After exposure to the activating radiation or sunlight for approximately 30 minutes, section B of the representation shows that the transmittance of light through the lens at the top starts at about 10% and extends generally along the transmittance curve to the bottom where there is approximately the same transmission as shown in the bottom for the non-activated lens of section A.

We teach a method of making an ophthalmic quality lens having reversible, progressive, local variation in photochromic behavior. Such a lens includes a portion ultimately to serve as a distance portion 110 and another portion ultimately to serve as a near portion 111 (see FIGS. 1 and 4B). When such a lens is glazed, the darkest portion will be at the top 112 of the lens with the highest light transmission at the bottom 113 of the lens. The darkness and light transmission is substantially uniform laterally of such a lens. An important part of the invention is subjecting such a lens to a graded thermal masking. The thermal masking is comprised of a group of cooperating parts, or elements. As shown in FIG. 4, these cooperating elements are the sand bath 115, the asbestos strip 116, and a chromite fusing block 117. Looking at these numerals 115, 116, and 117, one can see that they together provide the maximum masking over that area of the lens 111 which is eventually to serve as the near portion with there being progressively less masking towards the exposed top edge 112 which defines the upper limit of the distance portion 110.

We teach a method of making an ophthalmic quality lens having reversible, progressive, local variation in photochromic behavior. Such a lens includes a portion ultimately to serve as a distance portion 110 and another portion ultimately to serve as a near portion 111 (see FIGS. 4 and 7B). When such a lens is glazed, the darkest portion will be at the top 112 of the lens with the highest light transmission at the bottom 113 of the lens. The darkness and light transmission is substantially uniform laterally of such a lens. An important part of the invention is subjecting such a lens to a graded thermal masking. The thermal masking is comprised of a group of cooperating parts, or elements. As shown in FIG. 4, these cooperating elements are the sand bath 115, the asbestos strip 116, and a chromite fusing block 117. Looking at these numerals 115, 116, and 117, one can see that they together provide the maximum masking over that area of the lens 111 which is eventually to serve as the near portion with there being progressively less masking towards the exposed top edge 112 which defines the upper limit of the distance portion 110.

Having thus described my invention in detail with sufficient particularity as to enable one skilled in the art to practice the invention, what is desired to be protected by letters patent is set forth in the following claims:

1. A method of making ophthalmic lenses with a reversible progressive gradient photochromic behavior with a continuous variation of transmissivity in a heat treatment furnace from a lens blank composed of potentially phototropic or photochromic glass containing all the necessary ingredients including uniformly dispersed silver halide therein to develop photochromic or phototropic behavior during heat treatment including the steps of thermally masking a portion of said lens blank to substantially inhibit the development of photochromic or phototropic behavior in the masked portion and heating the lens blank in the heat treatment furnace to a temperature in the unmasked portion to develop photochromic or phototropic behavior therein and suppressing the transmission of furnace heat by the masking and maintaining a progressive heat gradation in said lens blank so that progressive gradient photochromic behavior and a continuous varying transmissivity is produced therein, wherein the improvement comprises:
   (a) mounting a lens blank in a carrier for heat treatment;
   (b) placing a dam adjacent said lens blank proximate the region between the masked portion of said lens blank and the unmasked portion thereof;
   (c) masking a portion of said lens blank by placing particulate material on one side of said dam so as to cover said portion of said lens blank whereby during heating of said lens blank in said heat treatment furnace to a temperature in the unmasked portion to develop photochromic behavior therein and suppressing the transmission of furnace heat by said masking and maintaining a progressive heat gradation in said lens blank so that progressive gradient photochromic behavior in a continuous varying transmissivity is produced therein.

2. The improvement according to claim 1 wherein the particulate material for masking is glass makers silica.

3. The improvement according to claim 1 wherein said lens blank is mounted on a fusing block.

4. The improvement according to claim 1 wherein a spaced series of lens blanks are mounted in said carrier and arranged generally parallel and placing a body of particulate material in the space between adjacent dams to mask adjacent portions of said lens blanks in the series and leaving portions of the lens blanks on opposite sides of the dams unmasked.

5. The improvement according to claim 4 wherein said spaced series of glass members are mounted on said spaced fusing blocks.

6. The improvement according to claim 1 wherein said masked lens blank is heated in the unmasked portion to about 1220° F. and then cooled to ambient temperature in a period of about 90 minutes wherein said temperature in said unmasked portion is held at a temperature about 1220° F. for a period of 20–30 minutes.

* * * * *